United States Patent [19]

Kunt et al.

[11] Patent Number: 6,095,681

[45] Date of Patent: Aug. 1, 2000

[54] METHOD FOR OPERATING A SENSOR TO DIFFERENTIATE BETWEEN ANALYTES IN A SAMPLE

[75] Inventors: Tekin Kunt, Houston, Tex.; Richard E. Cavicchi, Washington Grove, Md.; Stephen Semancik, Mt. Airy, Md.; Thomas J. McAvoy, Arnold, Md.

[73] Assignee: The United States of America as represented by the Secretary of Commerce, Washington, D.C.

[21] Appl. No.: 09/123,510

[22] Filed: Jul. 28, 1998

[51] Int. Cl.[7] .......................... G01N 25/36; G01N 25/46; G01N 27/00; G01N 27/12; G01N 27/14

[52] U.S. Cl. .................................. 374/45; 374/4; 374/10; 374/15; 374/43; 374/101; 374/102; 374/137; 73/31.06; 73/23.2; 73/1.02

[58] Field of Search ................................. 374/45, 4, 10, 374/15, 43, 101, 102, 137; 73/1 G, 31.06, 23, 25.01; 340/632–634

[56] References Cited

U.S. PATENT DOCUMENTS

| | | | |
|---|---|---|---|
| 3,898,837 | 8/1975 | Boege | 73/23.1 |
| 3,906,473 | 9/1975 | Le Vine | 340/237 |
| 4,399,684 | 8/1983 | Advani et al. | 73/1 |
| 4,446,718 | 5/1984 | Bukowiecki et al. | 73/23 |
| 4,567,475 | 1/1986 | Bukowiecki et al. | 73/23 |
| 4,627,269 | 12/1986 | Forster et al. | 73/23 |
| 4,638,443 | 1/1987 | Kaneyasu et al. | 364/497 |
| 4,670,405 | 6/1987 | Stetter et al. | 436/151 |
| 4,847,783 | 7/1989 | Grace et al. | 364/497 |
| 5,106,756 | 4/1992 | Zaromb | 436/161 |
| 5,198,988 | 3/1993 | Dorr et al. | 364/497 |
| 5,345,213 | 9/1994 | Semancik et al. | 257/253 |
| 5,400,643 | 3/1995 | De Angelis et al. | 73/31.06 |
| 5,464,966 | 11/1995 | Gaitan et al. | 219/544 |
| 5,521,908 | 5/1996 | Younce et al. | 370/32.1 |
| 5,526,280 | 6/1996 | Consadori et al. | 364/496 |
| 5,528,225 | 6/1996 | Sakai et al. | 340/632 |
| 5,573,728 | 11/1996 | Loesch et al. | 422/90 |
| 5,635,628 | 6/1997 | Fleischer et al. | 73/31.06 |

OTHER PUBLICATIONS

Rattan et al.; A comparative study of signal processing techniques for clustering microsensor data (a first step towards an artificial nose); Feb., 1997; pp. 105–120.

Kunt et al.; Dynamic Modeling and Optimization of Micro–Hotplate Chemical Gas Sensors; Jun. 1997; pp. 91–95.

Steve Semancik and Richard Cavicchi; Kinetically Controlled Chemical Sensing Using Micromachined Structures; Jun. 1998; pp. 279–287.

*Primary Examiner*—G. Bradley Bennett
*Assistant Examiner*—Gail Verbitsky
*Attorney, Agent, or Firm*—Leydig, Voit & Mayer, Ltd.

[57] ABSTRACT

Disclosed is a method for operating a sensor to differentiate between first and second analytes in a sample. The method comprises the steps of determining a input profile for the sensor which will enhance the difference in the output profiles of the sensor as between the first analyte and the second analyte; determining a first analyte output profile as observed when the input profile is applied to the sensor; determining a second analyte output profile as observed when the temperature profile is applied to the sensor; introducing the sensor to the sample while applying the temperature profile to the sensor, thereby obtaining a sample output profile; and evaluating the sample output profile as against the first and second analyte output profiles to thereby determine which of the analytes is present in the sample.

10 Claims, 4 Drawing Sheets

METHOD FOR OPERATING A SENSOR TO DIFFERENTIATE BETWEEN ANALYTES IN A SAMPLE

TECHNICAL FIELD OF THE INVENTION

The invention is in the field of sensors and methods for sensor control. The invention finds particular applicability in the field of microhotplate sensors.

BACKGROUND OF THE INVENTION

Thermally controllable microhotplate sensors for gases and vapors are known in the art. Examples of such microhotplate sensors are disclosed in U.S. Pat. Nos. 5,464,966 and 5,345,213. Such sensors typically comprise a support substrate, a heating element thermally isolated from the substrate, a conductive heat distribution plate formed above the heating element, and a layer of a chemically active material formed above the heat distribution plate. The sensors are characterized by having a low mass (on the order of about 0.2 $\mu$g) such that the temperature of the sensor can be controlled over a wide range (on the order of 20° C. to about 1200° C.) and changed very rapidly (with rise times on the order of about 1 msec). These sensors can be formed into an array, the individual sensors constituting "pixels" or elements in the sensor array.

Further details concerning the function and operation of the foregoing sensors can be found in the aforementioned U.S. Pat. Nos. 5,345,213 and 5,464,966 and in Cavicchi et al., "Fast Temperature Programmed Sensing for Micro-Hotplate Gas Sensors," *IEEE Electron Device Letters* 16(3):1–3 (1995) and in Suehle et al., "Tin Oxide Gas Sensor Fabricated Using CMOS Micro-Hotplates and in-situ processing," *IEEE Electron Device Letters* 14(3):118–120 (1993). For present purposes, it is sufficient to state that the chemically active material in such sensors interacts with a detected analyte, thus causing a change in the conductance of the chemically active material. The change in conductance of the chemically active material thus may be used to detect the presence of the analyte.

While such sensors are useful in detecting the presence or absence of a single analyte, it can be more difficult for the sensor to differentiate between two or more analytes, especially when the analytes are chemically similar. For example, when the sensor is operated with a linear temperature profile that is pulsed, i.e., cyclically varied, the conductance output profile over time of the sensor for a first analyte (for example, methanol) often is very similar to that for a second, chemically similar analyte (for example, ethanol). When the sensor is introduced to an unknown sample containing one or both of the first and second analytes, it thus can be difficult for the operator to differentiate between the first and the second analytes based on the sensor output profile obtained.

It is a general object of the invention to provide a method and apparatus for operating a sensor, such as a microhotplate and apparatus, to enhance the difference between the output profiles of the sensor when introduced to first and second analytes to thereby assist an operator in differentiating between first and second analytes in a sample of unknown composition. A further general object is to provide a method and apparatus for operating a sensor in which the detection time is minimized while still enhancing the difference in the sensor output profiles as between the first and second analytes.

SUMMARY OF THE INVENTION

It has now been found that the output profile of a microhotplate or other thermally variable sensor depends on the temperature at which the sensor is operated, the rate of pulsing of the sensor, and other factors. It has further been found that the output profile of the sensor for one analyte may be caused to vary substantially from that for another analyte, depending upon the temperature profile applied to the sample. In accordance with the invention, an optimized temperature or other suitable input profile is determined and is applied to the sensor. The optimized input profile is an input profile, not necessarily unique, that will enhance the difference between the output profiles of the sensor as between first and second analytes present or potentially present in an unknown sample compared to a linearly ramped input temperature profile or other non-optimized profile. This optimized input profile is applied to the sensor as the sensor is introduced to an unknown sample, and the output profile of the sensor is evaluated against known sensor output profiles of the first and second analytes to thereby determine which of the analytes is present in the sample.

In accordance with a preferred embodiment of the invention, the optimized temperature profile is determined for a microhotplate sensor by modeling the output profile of the sensor for each of the first and second analytes. Any number of modeling methods may be employed in conjunction with the invention, and preferred methods include models based on neural networks or wavelet networks. The temperature profile may be modeled for any arbitrarily chosen input temperature profile. Upon modeling of the output profile, an optimized temperature profile may be calculated in accordance with conventional methods. In accordance with a highly preferred embodiment of the invention, the sensor detection time is minimized by determination of the minimum pulse duration and minimum number of pulses that will result in enhancement of the difference in the output profiles of the sensor as between the first and second analytes to a predetermined degree.

Other features and advantages of the invention will be apparent from the following drawings and description of the invention.

DESCRIPTION OF THE INVENTION

The invention is described herein particularly with respect to microhotplate sensors. It should be understood, however, that the invention is applicable more broadly to any type of sensors wherein a sensor output profile is controlled by an input profile. Examples include Taguchi-type or calorimetric sensors, where an input temperature is varied over time to define a temperature profile, and amperometric sensors, where an input voltage is varied over time to define a voltage profile. The input temperature may be applied and varied by conventional means. The term "sensor" is further contemplated to be any apparatus or device that may be used to analyze or detect any liquid, vapor, solid, gaseous material, or other physical object. Moreover, while the invention is described herein with respect to analytes in vapor form, it should be understood that the invention is contemplated as being applicable to the detection and differentiation of any liquid, vapor, solid, or gaseous material or other physical objects. It is further contemplated that such analytes may be present in any media in which the sensor for sensing such analytes is operable, such as gaseous or liquid media. The invention is further contemplated to be applicable both when the sample includes either one analyte to the exclusion of the other analyte, and when the sample includes a mixture of two analytes. In either case, the sensor may be employed to sense the presence of a first analyte in a mixture of two analytes wherein the presence of the second analyte is considered as "noise" which interferes with the detection of the first analyte.

Figure 1:
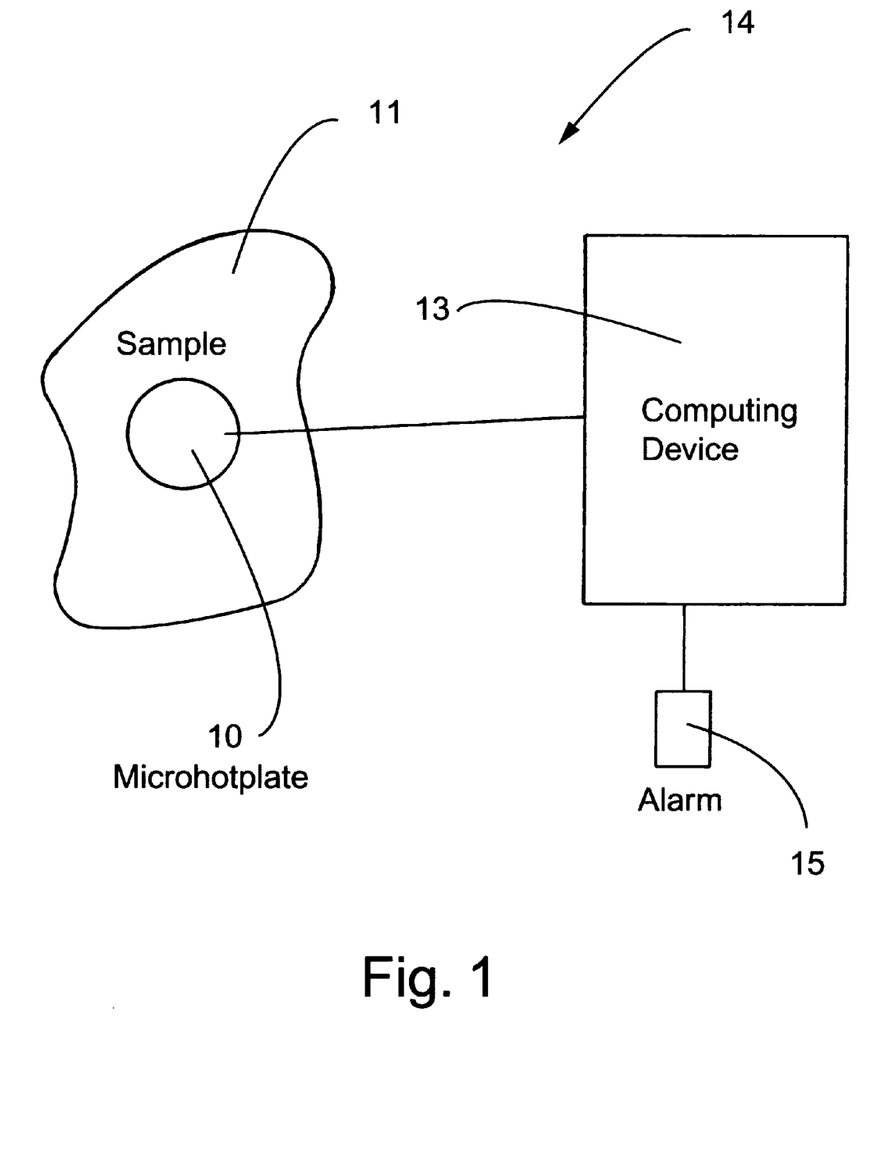
FIG. 1 is a schematic view of a microhotplate sensor as it is applied to a sample of unknown composition.

Turning now to FIG. 1, a microhotplate sensor is shown generally at 10. The sensor 10 is in communication with a sample 11, which sample includes one or more analytes to be detected. The sensor may communicate with a processor or other computing means 13. The computing means 13 and the sensor 10 define a sensor system 14. The computing means and/or the sensor may be connected to an alarm 15 or other output mechanism, which may be set to activate upon detection of the first analyte. In such case, it is desirable for the operator or controlling computer to be able to differentiate between the first analyte, which would desirably cause activation of the alarm 15, and the second analyte, for which the alarm should not be triggered. If the sensor is not able to differentiate between the first and second analytes, the sensor system 14 may report a false alarm. The temperature rise and fall in the sensor is driven by the processor or in another suitable manner, as is known in the art.

Figure 2:
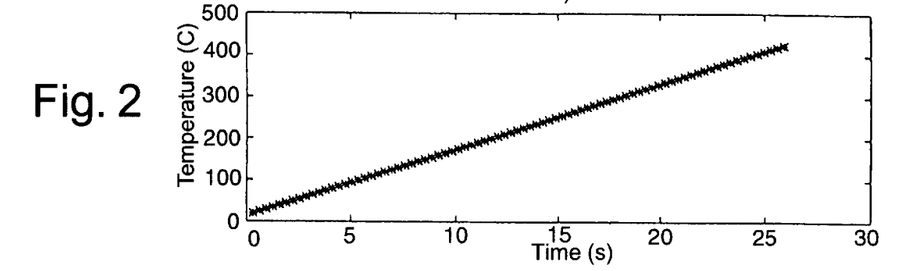
FIG. 2 is a graphical representation of a linearly ramped temperature profile as it is applied to the sensor of FIG. 1. Such linearly ramped profile is typical of prior art sensor operation.
Figure 2A:
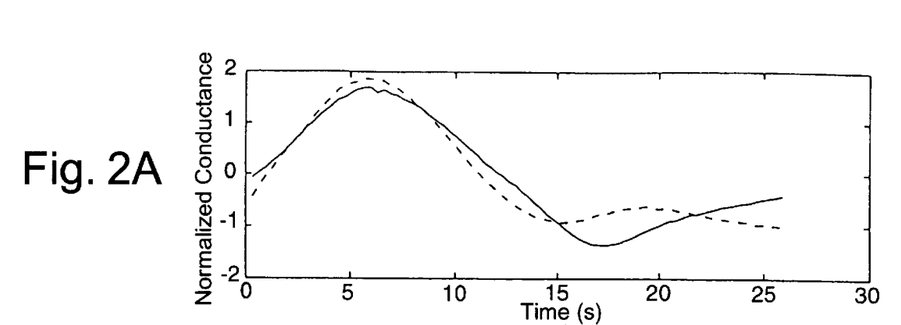
FIG. 2A is a graphical representation of the conductance output profile of the sensor, shown for both methanol and ethanol, when the temperature profile shown in FIG. 2 is applied to the sensor.
Figure 2B:
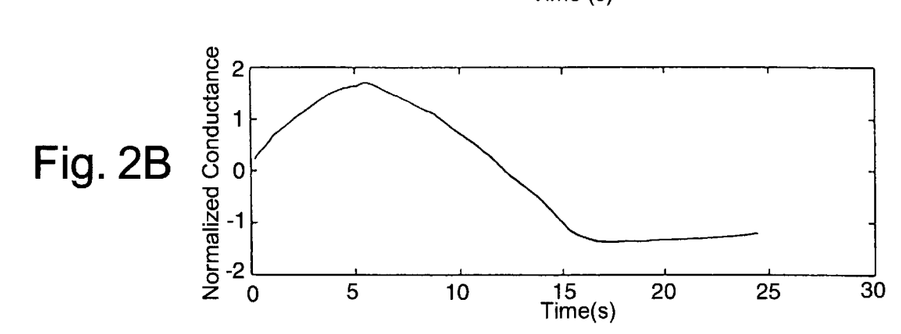
FIG. 2B is a graphical representation of the conductance output profile of the sensor for a sample of unknown composition.

FIGS. 2 and 2A together illustrate operation of a sensor in the detection of methanol and ethanol prior to calculation of an optimum temperature profile. A microhotplate sensor was introduced to samples of methanol and ethanol in vapor form. Each sample included approximately 1% methanol or ethanol in air. The temperature of the sensor was pulsed in a linear ramp between about 20° C. and 425° C. over about 26 seconds, as shown in FIG. 2, and the conductance output of the sensor was evaluated for methanol (solid line in FIG. 2A) and ethanol (dashed line in FIG. 2A). As shown therein, the conductance output profile of the sensor for methanol is substantially similar to the conductance output of the sensor for ethanol. If the temperature profile of the sensor were ramped linearly when the sensor was introduced to a sample of unknown composition, an output profile generally resembling that of FIG. 2B likely would be obtained. From this profile, it would be difficult to determine the composition of the sample, inasmuch as the profile of FIG. 2B resembles that of both methanol and ethanol.

In accordance with the invention, an optimized temporal temperature or other input profile is determined. The optimized temperature profile is a profile which will enhance the difference between the output profiles of the sensor for the first analyte and for the second analyte as compared with a non-optimized profile, such as a non-optimized linearly ramped input profile. The difference between the output profiles may be qualitatively evaluated, or may be quantitatively determined by suitable techniques. In one embodiment, the difference is evaluated via calculation of the normalized sum of the squared differences (NSSD) between the sensor output profiles according to the following equation.

$$NSSD = \frac{1}{n}\sum_{i=1}^{n}(y^1 - y^2)^2$$

In this equation, $y^1$ is the temporal conductance output profile for the first analyte and is an n-component vector with n values of conductance output profile generated sequentially as a result of n values in the input temperature profile, and thus expressed as the conductance of the sensor as a function of time $y^2$ is the temporal conductance output profile for the second analyte; and n is the number of temperature pulses in a given cycle of sensor operation.

The input temperature profile is "enhanced" by determining a temperature profile that will allow an operator or the sensor system to differentiate between the first and second analytes in a sample of unknown composition. The temperature profile thus obtained may be described as an "optimized" temperature profile. It should be understood that, for any given first and second analytes, there may be one or several temperature profiles that may be described as "optimized" for differentiation between the analytes.

To obtain an optimized temperature profile, the sensor is first "trained" using the first and second analytes and the conductance output profile determined over a wide range of sensor conditions. Data from the sensor is gathered for forming a data-based model. The collected data from the sensor output is then modeled for each analyte on the training data for each of the analytes, and an optimized temperature profile then is determined based upon the models. The conductance output of the sensor will depend on the previous conductance values and temperature history of the sensor, and may be expressed according to the following function:

$$G_{i+1} = F(G_i, G_{i-1}, \ldots G_{i-(n_y-1)}; U_{i+1}, U_i, \ldots U_{i-(n_s-2)})$$

wherein G is the conductance of the sensor, i is the incremental time value, U is the temperature of the sensor, and $n_y$ and $n_u$ are the model orders for the sensor. The conductance of the sensor as measured at a given time increment will vary in accordance with the conductance and temperature of the sensor as observed for some number of previous readings, the exact number depending on the material of the sensor and particular analytes. The sensor thus may be said to experience a "time lag," by which is meant that past sensor operation affects future sensor performance for some subsequent time period. Model orders $n_y$ and $n_u$ account for the consideration in the calculation of conductance G of previous conductance and temperature values that bear on sensor time lag.

The training of the sensor is conducted to determine the parameters of the conductance function for each of the analytes. To train the sensor, the sensor preferably is introduced to a sample of known composition, and behavioral data for the sensor then is taken. Preferably, the sensor is pulsed with a plurality of temperature pulses over a predetermined temperature range and predetermined cycle time. The preferred manner of temperature pulsing comprises applying a temperature pulse with a relatively short rise time (for example, about 1 ms); holding the pulsed temperature for a relatively long duration (about 10 ms to about 300 ms); cooling the sensor over a relatively short cooling period (about 1 ms); and waiting for an intermediate delay period duration (about 5 ms); and measuring the conductance of the sensor at the conclusion of the delay period, prior to the start of the next temperature pulse. The total time required for these operations defines a pulse duration.

The sensor is pulsed in this manner for a plurality of pulses stepwise in a linear fashion over a given temperature range. Preferably, the sensor is so pulsed over at least five temperatures within the range; more preferably, the sensor is pulsed over about ten temperatures. The temperature range for the first cycle is determined, for example, pseudorandomly by selecting a starting and finishing temperature within the sensor's operating range. To insure that the sensor response is not affected by temperature effects, the finishing temperature for a given future cycle is selected as the starting temperature for the successive cycle, the finishing temperature for the future cycle being selected at random. To ensure that the range of the sensor is not exceeded in any cycle, the maximum temperature difference between pulses is selected to be no greater than $$R_s/n$$

where $R_s$ is the range of operating temperatures (usually ambient temperature up to the maximum temperature of the sensor) and n is the number of pulses in the cycle. The maximum temperature difference between pulses also should be limited to about 40° C. to prevent changes in the sensor surface condition that will disrupt the modeling. This training is repeated over a predetermined number of cycles, preferably at least about 100 cycles, more preferably at least about 1,000 cycles, and even more preferably over at least about 5,000 cycles for each analyte. Data for the sensor, including sensor output at various temperature pulse slopes and endpoints, thus will be obtained.

After the sensor has been so trained for each analyte, a sensor model is developed based on the training data. The first step in the model is the determination of the lag times, or model orders $n_y$ and $n_u$. The model orders can be calculated using any suitable mathematical technique, such as the false nearest neighbors analysis, as described in Rhodes et al., "Determining the Model Order of Nonlinear Input/Output Systems Directly from Data," in *Proceedings of the American Control Conference*, Seattle, Wash. (June 1995) at 2190–94, and Bomberger et al., Estimation of Model Order from Input-Output Data Applied to Radial Basis Function Network Identification," in *Proceedings of the IFAC Symposium Adchem '97*, Banff, Canada (June 1997) at 31–36. Essentially, the false nearest neighbors approach assumes that the data values near to one another in the input space are also close to one another in the output space. If this assumption proves incorrect, for neighboring points, those points are labeled "false nearest neighbors." The percentage of these false nearest neighbors are calculated for each time delay in the input variables until the percentage of false neighbors drops to an acceptably low level. The determination of model orders thereby is within the level of ordinary skill in the art.

After selection of the model orders, a model structure is selected, and parameters for the model are determined. Any suitable technique for modeling the sensor output, such as regression techniques, may be employed in conjunction with the invention. Suitable model structures include, for example, linear autoregressive exogenous modeling (ARX), as described in Ljung, *System Identification: Theory for the User* (1987); neural network modeling, such as neural network partial least squares nonlinear autoregressive with exogenous inputs (NNPLS-NARX), as described in Qin et al., "Nonlinear FIR modeling Via a Neural Net PLS Approach," *Computers Chem Eng.* 20(2):147–59 (1996); or continuous time models, such as Runge Kutta Neural Net (NNRUNGE), as described in Rico-Martinez et al., "Discrete vs. Continuous Time Nonlinear Signal Processing of Cu Electrodissolution Data," *Chem. Engr. Comm.* 118:25–48 (1992). Preferably, however, wavelet networks, i.e., combinations of the wavelet transformation with neural networks, are used to model the sensor output. As described, for example in Zhang et al., "Wavelet Networks," *IEEE Trans. On Neural Networks* 3:889–98 (1992), wavelength functions, such as the so-called "Mexican Hat" wavelet, can be used to approximate any function to any desired level of accuracy. Wavelets are further well adapted for approximation of abruptly changing functions. Because the sensor output profile values from microhotplate sensors can change abruptly over time, wavelets thus find particular applicability in connection with the present invention. Further details concerning wavelet networks may be found in Zhang, "Using wavelet networks in nonparametric estimation," *Technical Report* 833, IRISA (1994).

After models have been determined for each of the first and second analytes, an optimized temperature profile for the sensor is determined. Any suitable method can be used for calculating such optimized temperature profile, such as Quadratic Programming. The optimized profile may be obtained, for example, using the Sequential Quadratic Programming (SQP) algorithm found in the MATLAB Optimization Toolbox, a computer program library. Further details concerning the SQP algorithm may be found, for example, in Kunt et al., "Towards the Development of an Artificial Nose for Chemical Process Applications," *Computers Chem. Eng.* 20:S1437–42 (1996). The conductance output profiles for the sensor for each of the first and second analytes at the optimized input temperature profile are then determined, either by predicting the profiles based on the optimized temperature profile obtained, or, more preferably, by introducing the sensor to samples of each analyte and observing the conductance output profile in each case.

Figure 3:
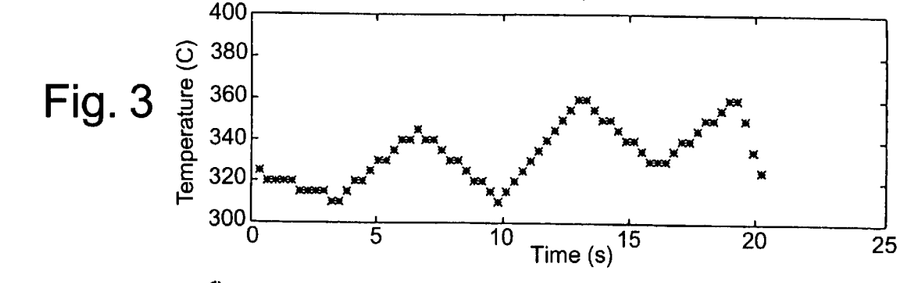
FIG. 3 is a graphical representation of an optimized temperature profile as it is applied to the sensor of FIG. 1.
Figure 3A:
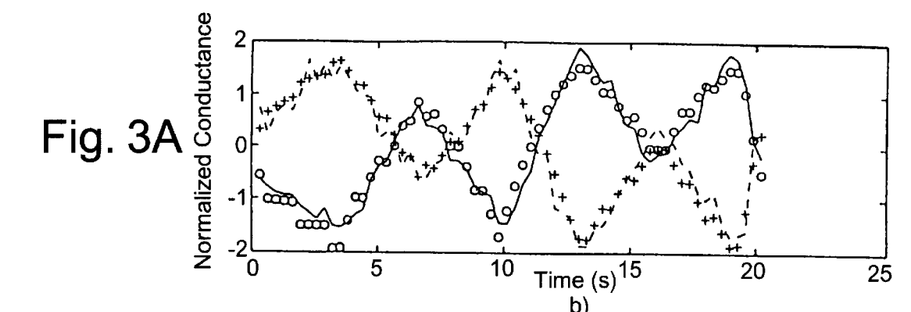
FIG. 3A is a graphical representation of the predicted and actual conductance output profiles of the sensor, shown for both methanol and ethanol, when the temperature profile shown in FIG. 3 is applied to the sensor.

FIG. 3 illustrates an optimized temperature profile, as determined for the sensor whose behavior is represented in FIGS. 2 and 2A. FIG. 3A illustrates the sensor conductance output profile for each of methanol (solid line) and ethanol (dashed line) when the optimized temperature profile is applied to the sensor. Predicted output profiles also are shown in FIG. 3A (the circles representing the predicted output profile for methanol and the pluses representing that for ethanol). It is seen that the conductance output profile for methanol is markedly distinct as compared to that for ethanol, especially in comparison to the output profiles observed when the linear temperature ramp of FIG. 2 is applied.

To analyze a sample of unknown composition, the sensor is introduced to the sample, and the optimized temperature profile is applied to the sensor. The output conductance profile of the sensor then is obtained and is evaluated against the output profiles that have been determined for the first and second analytes. For example, based on the output profile shown in FIG. 3B, the operator or sensor system could, by evaluation against the profiles shown in FIG. 3A, determine that the analyte likely is methanol.

Figure 4:
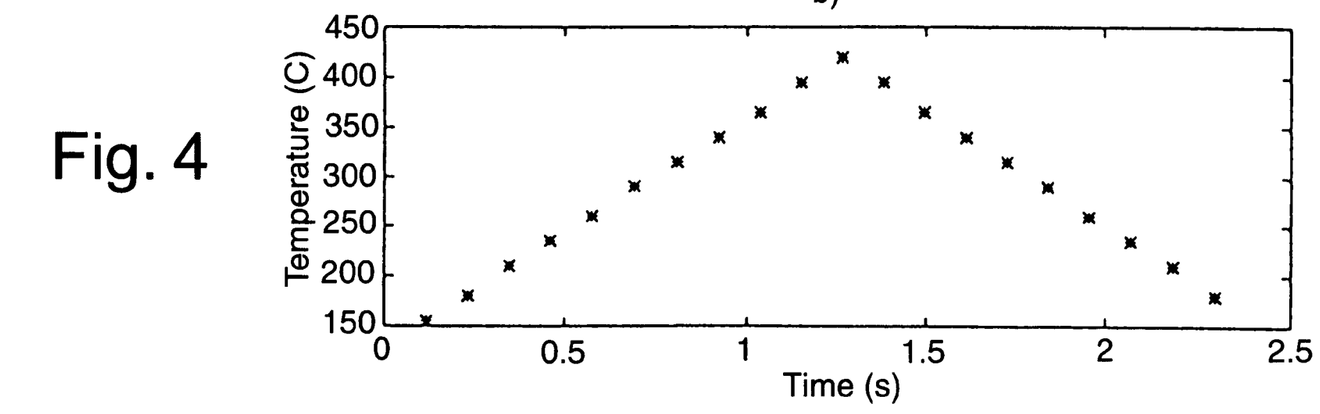
FIG. 4 is a graphical representation of an optimized temperature profile, calculated for twenty pulses and $NSSD_{minimum}=1$.
Figure 4A:
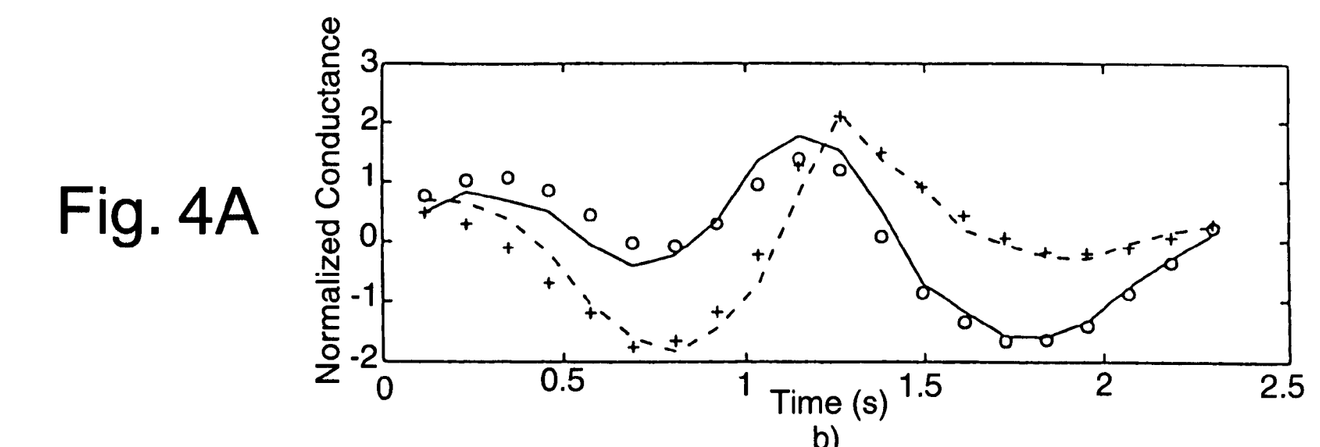
FIG. 4A is a graphical representation of the conductance output profile of the sensor, shown for both ethanol and ethanol, when the temperature profile shown in FIG. 4 is applied to the sensor (NSSD ($y^{MeOH}, y^{EtOH}$)=1.28).

In a preferred embodiment of the invention, the method further includes the step of determining an optimum temperature profile for a minimum cycle length. The minimum cycle length is determined by defining a metric for differentiating between the output profiles for the conductance curves, and assigning a minimum operating value for that metric. For example, when the metric chosen is the NSSD, a preferred minimum value may be at least about 0.5, and more preferably, the minimum value is about 1.0. After choosing the metric and minimum value, a minimum pulse duration is chosen to be longer than the thermal rise time of the sensor, but short enough to allow many pulses to be applied. The optimization of the temperature profile then is carried out for a data set including a plurality of data pulse values, the data pulse values and minimum pulse duration defining a cycle for the temperature optimization. The minimum number of pulses that provide conductance profiles for the first and second analytes wherein the metric has at least the predetermined minimum value will provide the optimized temperature profile of minimum length. FIGS. 4 and 4A illustrate respectively the optimized temperature profile of minimum length, determined where $NSSD_{minimum}=1$. For this sensor, the minimum number of pulses per cycle was found to be 20, a cycle that yields conductance profiles y for methanol and ethanol wherein NSSD ($y^{methanol}$, $y^{ethanol}$)=1.28.

The following Example illustrates the method of the invention, but should not be construed as limiting in scope.

EXAMPLE

In this Example, a microhotplate sensor having a polysilicon resistor, an aluminum hotplate for distributing heat, and a $SnO_2$ sensing film was operated to differentiate between methanol and ethanol vapor. The sensor was operable between room temperature (approximately 25° C.) and 425° C.

I. TRAINING

For each of the methanol and ethanol analytes, the sensor was trained over 1,000 temperature pulse cycles at which the conductance output of the sensor was measured. To obtain a conductance measurement, a temperature range was selected at random, and the sensor temperature was pulsed stepwise over ten steps within the range. For each temperature step, the sensor was brought to the desired temperature in a time interval of about 1 ms, held at the desired temperature for about 100 ms, allowed to drop to room temperature, the drop taking about 1 ms, and held at room temperature for about 5 ms before recording the conductance of the sensor. The data obtained was stored in a file on a computer and transferred to a SPARC System 1 workstation.

II. MODELING

Mexican hat wavelets with up to four scale levels were used to model the sensor. The initial model structure was synthesized using stepwise selection by the orthogonalization procedure, as described in Chen et al., "Orthogonal least squares methods and their application to non-linear system identification," *Int. J. Control* 50(5): 1873–96 (1989). The procedure involved selection of 88 out of 247 possible wavelets. The initial model was further trained for four epochs using the Gauss-Newton method.

III. MODEL VALIDATION

One thousand data points were used to validate the model. The normalized mean squared error (defined as the sum of the squared differences between the actual and predicted conductance values, divided by the number of test samples and the variance of the conductance values in the test sample) was 0.0459, a value that was sufficiently low to indicate that the model was satisfactory.

To confirm whether the operating conditions of the sensor are consistent with the operating conditions of the sensor during the training, multivariate tools such as principal component analysis (PCA), as described in Negiz et al., "Monitoring of multivariable dynamic processes and sensor auditing," *Proceedings of the IFAC Symposium Adchem* 1997, 55–60 (June, 1997), may be used. Hypothesis tests such as squared prediction error (SPE) and Hotelling's $T^2$ test may be used to measure the change in the correlation structure and to detect any change in operating conditions, respectively.

IV. DETERMINATION OF OPTIMUM TEMPERATURE PROFILE

The sensor was optimized, off-line, by using the Sequential Quadratic Programming (SQP) algorithm provided in the MATLAB Optimization Toolbox. The temperature profile of FIG. 3 was obtained.

V. DETERMINATION OF SENSOR OUTPUT

The temperature profile of FIG. 3A was applied to the sensor, and the sensor was applied to known samples of methanol and ethanol to yield the output profiles shown in FIG. 3A.

VI. TESTING OF UNKNOWN SAMPLE

Figure 3B:
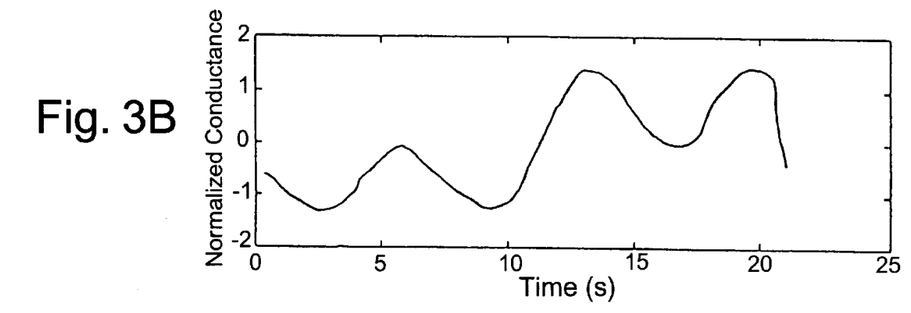
FIG. 3B is a graphical representation of the conductance output profile of the sensor for a sample of unknown composition.

The sensor is applied to a sample of unknown composition, and the output profile of FIG. 3B is obtained. By comparing the output profile to those shown in FIG. 3A, it is determined that the sample includes methanol.

VII. DETERMINATION OF MINIMUM CYCLE TIME

A minimum pulse duration of 100 ms was chosen, and a data set of pulses consisting of the following number of temperature pulses per cycle was chosen.

n=16
n=20
n=40
n=58
n=64

For each of the foregoing number of pulses, an optimum temperature profile was determined as set forth above, and sensor output profiles for methanol and ethanol were observed upon application of the input temperature profiles to the sensor. The NSSD for the sensor output profiles in each case was determined, with the minimum acceptable NSSD being selected as 1.0. The following results were obtained:

| n | cycle duration (seconds) | NSSD |
|---|---|---|
| 16 | 1.84 | 0.66 |
| 20 | 2.30 | 1.28 |
| 40 | 4.60 | 0.36 |
| 58 | 6.67 | 2.66 |
| 64 | 7.36 | 1.29 |

The minimum number of pulses yielding sensor output profiles for methanol and ethanol with an NSSD of at least 1.0 was 20. FIG. 4 illustrates the input temperature profile obtained for n=20, and FIG. 4A illustrates the corresponding output profile of the sensor.

It is thus seen that the foregoing general objects have been satisfied. The invention provides a sensor apparatus and method for operating a sensor that overcomes the drawbacks of prior art methods. When the sensor apparatus is operated as described above, an optimized temperature profile may be calculated and the difference between the output profiles of the sensor as between two analytes enhanced. The invention can further be used to minimize the cycle length for the sensor for any assigned output profile differentiation metric value.

While particular embodiments of the invention have been shown, it will be understood that the invention is not limited thereto since modifications may be made by those skilled in the art, particularly in light of the foregoing teachings. For example, while the invention has been described particularly with reference to sensor output conductance profiles in a temperature ramped sensor, the invention is not limited thereto, but rather finds applicability with other profiles and measurements. It is, therefore, contemplated by the appended claims to cover any such modifications as incorporate those features which constitute the essential features of these improvements within the true spirit and scope of the invention. All references cited herein are hereby incorporated by reference in their entireties.

What is claimed is:

1. A method for operating a sensor to differentiate between first and second analytes in a sample, said sensor being capable of having a variable temperature profile applied thereto and said sensor generating an output profile upon sensing an analyte, the method comprising the steps of:
    determining a temperature profile for said sensor which will enhance the difference in the output profiles of the sensor as between the first analyte and the second analyte;
    determining a first analyte output profile as observed when said temperature profile is applied to said sensor;
    determining a second analyte output profile as observed when said temperature profile is applied to said sensor;
    introducing said sensor to said sample while applying said temperature profile to said sensor;
    obtaining a sample output profile; and
    evaluating said sample output profile as against said first and second analyte output profiles to thereby determine whether said first or said second analyte is present in said sample.

2. A method according to claim 1, wherein said step of determining said temperature profile includes the steps of determining a first sensor model for said first analyte, said first sensor model predictive of an output profile of the sensor as a function of the temperature of the sensor; and determining a second sensor model for said second analyte, said second sensor model predictive of an output profile of the sensor as a function of the temperature of the sensor.

3. A method according to claim 2, wherein said steps of developing said sensor models each include the steps of:
    (1) determining a first temperature;
    (2) determining a second temperature, the difference between said first and second temperatures defining a thermal range;
    (3) pulsing the temperature of said sensor from said first temperature to a plurality of intermediate temperatures over said thermal range over a predetermined time period, at each of said intermediate temperatures allowing the temperature of said sensor to return to a measurement temperature;
    (4) determining an output value for said sensor at said measurement temperature; and
    (5) repeating steps (1)–(4) for a plurality of cycles.

4. A method according to claim 3, each of said cycles being repeated over a time period equal to said predetermined time period.

5. A method according to claim 3, the first temperature in a given cycle being identical to the second temperature from an immediately preceding cycle, wherein said second temperature for said given cycle is determined randomly.

6. A method according to claim 3, further comprising the step of calculating a minimum temporal profile period by the steps of:
    selecting a minimum pulse duration;
    selecting a data set including a plurality of pulse numbers;
    for each of said pulse numbers;
        determining a temperature profile for said sensor which will enhance the difference in the output profiles of the sensor as between the first analyte and the second analyte;
        observing a first analyte output profile as observed when said temperature profile is applied to said sensor;
        observing a second analyte output profile as observed when said temperature profile is applied to said sensor; and
    determining for said data set the minimum pulse number that allows for differentiation between said first analyte and said second analyte.

7. A method according to claim 6, wherein said minimum pulse number is determined in accordance with the following relationship:

$$NSSD(y^1, y^2) \geq 1$$

wherein $y^1$ is the sensor output profile for the first analyte and $y^2$ is the sensor output profile for the second analyte.

8. A method according to claim 1, wherein said sensor is a microhotplate sensor, wherein said output profiles for said first and second analytes comprise conductance output profiles.

9. A method according to claim 1, further comprising the step of activating an alarm if said first analyte is detected in said sample.

10. A method for operating a sensor to differentiate between first and second analytes in a sample, said sensor being capable of having a variable input profile applied thereto and said sensor generating an output profile upon sensing an analyte, the method comprising the steps of:
    determining an input profile for said sensor which will enhance the difference in the output profiles of the sensor as between the first analyte and the second analyte;
    determining a first analyte output profile as observed when said input profile is applied to said sensor;

determining a second analyte output profile as observed when said input profile is applied to said sensor;

introducing said sensor to said sample while applying said input profile to said sensor, thereby obtaining a sample output profile;

evaluating said sample output profile as against said first and second analyte output profiles to thereby determine whether said first or said second analyte is present in said sample.

* * * * *